United States Patent
Krimsky

(10) Patent No.: US 11,737,827 B2
(45) Date of Patent: *Aug. 29, 2023

(54) PATHWAY PLANNING FOR USE WITH A NAVIGATION PLANNING AND PROCEDURE SYSTEM

(71) Applicant: Covidien LP, Mansfield, MA (US)

(72) Inventor: William S. Krimsky, Forest Hill, MD (US)

(73) Assignee: Covidien LP, Mansfield, MA (US)

( * ) Notice: Subject to any disclaimer, the term of this patent is extended or adjusted under 35 U.S.C. 154(b) by 616 days.

This patent is subject to a terminal disclaimer.

(21) Appl. No.: 16/853,931

(22) Filed: Apr. 21, 2020

(65) Prior Publication Data
US 2020/0246076 A1 Aug. 6, 2020

Related U.S. Application Data

(63) Continuation of application No. 15/253,409, filed on Aug. 31, 2016, now Pat. No. 10,631,933.

(51) Int. Cl.
*A61B 34/10* (2016.01)
*G16H 50/50* (2018.01)
(Continued)

(52) U.S. Cl.
CPC .............. *A61B 34/10* (2016.02); *A61B 34/20* (2016.02); *G16H 20/40* (2018.01); *G16H 50/30* (2018.01);
(Continued)

(58) Field of Classification Search
CPC ................................ A61B 34/10; A61B 34/20
See application file for complete search history.

(56) References Cited

U.S. PATENT DOCUMENTS 7,822,461 B2 10/2010 Geiger et al.
7,985,187 B2 7/2011 Wibowo et al.
(Continued)

OTHER PUBLICATIONS

Bergeles, C.; Gosline, A. H.; Vasilyev, N. V.; Codd, P. J.; del Nido, P. J.; Dupont, P. E. Concentric Tube Robot Design and Optimization Based on Task and Anatomical Constraints. IEEE Transactions on Robotics 2015, 31 (1), 67-84.*
(Continued)

*Primary Examiner* — Soren Harward
(74) *Attorney, Agent, or Firm* — Carter, DeLuca & Farrell LLP

(57) ABSTRACT

Disclosed are systems, devices, and methods for planning a procedure for treatment of tissue in a patient's lungs. An exemplary method includes generating a three-dimensional (3D) model of the patient's lungs, displaying the 3D model of the patient's lungs, selecting a target location in the tissue of the patient's lungs as displayed on the 3D model, identifying a point on a pleural surface of the patient's lungs with access to the target location, determining an access path between the target location and the identified point on the pleural surface, calculating a risk of injury to intervening structures between the identified point on the pleural surface and the target location, based on the determined access path, and displaying the access path and the calculated risk of injury for the access path on the 3D model.

20 Claims, 9 Drawing Sheets

(51) Int. Cl.
*G16H 50/30* (2018.01)
*G16H 20/40* (2018.01)
*A61B 34/20* (2016.01)

(52) U.S. Cl.
CPC ........ *G16H 50/50* (2018.01); *A61B 2034/101* (2016.02); *A61B 2034/107* (2016.02)

(56) References Cited

U.S. PATENT DOCUMENTS

| | | |
|---|---|---|
| 8,218,846 B2 | 7/2012 | Trumer et al. |
| 8,494,246 B2 | 7/2013 | Trumer et al. |
| 8,611,983 B2 | 12/2013 | Glossop |
| 8,696,549 B2 | 4/2014 | Holsing et al. |
| 8,696,685 B2 | 4/2014 | Gilboa |
| 8,700,132 B2 | 4/2014 | Ganatra et al. |
| 9,259,290 B2 | 2/2016 | Jenkins et al. |
| 9,278,203 B2 | 3/2016 | Averbuch |
| 9,439,564 B2 | 9/2016 | Trumer et al. |
| 9,459,770 B2 | 10/2016 | Baker |
| 10,631,933 B2 | 4/2020 | Krimsky |
| 2005/0197558 A1 | 9/2005 | Williams et al. |
| 2006/0116576 A1 | 6/2006 | McGee et al. |
| 2007/0049861 A1 | 3/2007 | Gundel |
| 2008/0065109 A1 | 3/2008 | Larkin |
| 2008/0183073 A1 | 7/2008 | Higgins et al. |
| 2008/0234700 A1 | 9/2008 | Trovato et al. |
| 2009/0156895 A1 | 6/2009 | Higgins et al. |
| 2010/0121151 A1 | 5/2010 | Donhowe |
| 2010/0121316 A1 | 5/2010 | Weese |
| 2011/0015649 A1* | 1/2011 | Anvari .................. A61B 34/20 606/130 |
| 2011/0112549 A1 | 5/2011 | Neubach |
| 2011/0245625 A1 | 10/2011 | Trovato |
| 2012/0035540 A1* | 2/2012 | Ferren .................. A61B 5/076 604/95.01 |
| 2012/0059248 A1 | 3/2012 | Holsing et al. |
| 2014/0187949 A1 | 7/2014 | Zhao et al. |
| 2014/0343408 A1 | 11/2014 | Tolkowsky |
| 2014/0344742 A1 | 11/2014 | Wiemker et al. |
| 2015/0305650 A1 | 10/2015 | Hunter et al. |
| 2015/0351860 A1* | 12/2015 | Piron .................. A61B 5/0095 600/417 |
| 2015/0379760 A1 | 12/2015 | Averbuch et al. |
| 2016/0000303 A1 | 1/2016 | Klein et al. |

OTHER PUBLICATIONS

Kim, C.; Ryu, S. C.; Dupont, P. E. Real-Time Adaptive Kinematic Model Estimation of Concentric Tube Robots; IEEE: Hamburg, Germany, 2015; pp. 3214-3219.*

Torres, L. G.; Baykal, C.; Alterovitz, R. Interactive-Rate Motion Planning for Concentric Tube Robots; IEEE: Hong Kong, China, 2014; pp. 1915-1921.*

Berenson, D., Abbeel, P. & Goldberg, K. A robot path planning framework that learns from experience. In IEEE International Conference on Robotics andAutomation 3671-3678 (IEEE, 2012).

Kiraly, A. P., Helferty, J. P., Hoffman, E. A., McLennan, G. & Higgins, W. E. Three-dimensional path planning for virtual bronchoscopy. IEEE Transactions on Medical Imaging 23, 1365-1379 (2004).

Duriez, C., Gu, C., Marchal, M. & Cotin, S. Interactive Simulation of Flexible Needle Insertions Based on Constraint Models. In Medical Image Computing and Computer-Assisted Intervention (eds. Yang, G. Z., Hawkes, D., Rueckert, D., Noble, A. &Taylor, C.) 291-299 (Springer, Berlin, Heidelberg, 2009).

Caborni, C., Ko, S. Y., De Momi, E., Ferrigno, G. & Y Baena, F. R. Risk-based path planning for a steerable flexible probe for neurosurgical intervention. Proceedings of the IEEE RAS and EMBS International Conference on Biomedical Robotics andBiomechatronics 866-871 (2012).

International Written Opinion and Search Report for PCT/US2017/045837 dated Nov. 16, 2017 (10 pages).

* cited by examiner

PATHWAY PLANNING FOR USE WITH A NAVIGATION PLANNING AND PROCEDURE SYSTEM

CROSS-REFERENCE TO RELATED APPLICATIONS

This application is a continuation of U.S. application Ser. No. 15/253,409, filed Aug. 31, 2016.

FIELD

The present disclosure relates to the treatment of patients with lung diseases, and more particularly, to systems and methods for planning diagnostic and treatment procedures.

BACKGROUND

Lung cancer has an extremely high mortality rate, especially if it is not diagnosed in its early stages. In order to provide a diagnosis, a patient's lungs first undergoes imaging, for example, by using diagnostic tools such as computed tomography (CT) scans, to detect small lesions and nodules in the lung. Such scans may be used not only on those suspected of having the disease, but also on those at higher risk for early detection of the disease.

To confirm the diagnosis of the disease in the patient, biopsy and cytological examinations may be required to further identify the location and the extent to which these lesions and nodules are present before any treatment can be undertaken. In this regard, tools, such as bronchoscopes, biopsy devices, and the like, are navigated within the lungs to a treatment site. Using the biopsy device, the surgeon removes sample tissue from the lung at the treatment site to be tested and identified either as cancerous or non-cancerous. As biopsy is an invasive procedure, improvements are continually being sought to minimize trauma to the patient.

SUMMARY

Provided in accordance with the present disclosure is a method of planning a procedure for treatment of lung tissue. In an aspect of the present disclosure, the method includes generating a three-dimensional (3D) model of the patient's lungs, displaying the 3D model of the patient's lungs, selecting a target location in the tissue of the patient's lungs as displayed on the 3D model, identifying a point on a pleural surface of the patient's lungs with access to the target location, determining an access path between the target location and the identified point on the pleural surface, calculating a risk of injury to intervening structures between the identified point on the pleural surface and the target location, based on the determined access path, and displaying the access path and the calculated risk of injury for the access path on the 3D model.

In another aspect of the present disclosure, the identified point on the pleural surface is a first identified point on the pleural surface and the access path is a first access path, and the method further includes identifying a second point on the pleural surface with access to the target location, determining a second access path between the target location and the second identified point on the pleural surface, and calculating a risk of injury to intervening structures between the target location and the second identified point on the pleural surface, based on the determined second access path, and displaying the first access path and the calculated risk of injury for the first access path on the 3D model further includes displaying the second access path and the calculated risk of injury for the second access path on the 3D model.

In a further aspect of the present disclosure, the method further includes determining which of the first and second access paths has a lower calculated risk of injury, and selecting the access path that is determined to have a lower risk of injury.

In another aspect of the present disclosure, the method further includes receiving a user input selecting one of the first and second access paths.

In yet another aspect of the present disclosure, the point on the pleural surface with access to the target location is identified based on input received from a user.

In a further aspect of the present disclosure, identifying an alternative point on the pleural surface with access to the target location, determining an alternative access path between the alternative point on the pleural surface and the target location, and calculating a risk of injury to intervening structures between the target location and the alternative point on the pleural surface, based on the determined alternative access path, and displaying the access path and the calculated risk of injury for the access path on the 3D model further includes displaying the alternative access path and the calculated risk of injury for the alternative access path on the 3D model.

In another aspect of the present disclosure, the method further includes receiving a user input selecting a point on the target location as an end point for the access path, and the access path is determined between the identified point on the pleural surface and the point on the target location.

In a further aspect of the present disclosure, the method further includes identifying an alternative point on the target location as an alternative end point for the access path, determining an alternative access path between the identified point on the pleural surface and the alternative point on the target location, and calculating a risk of injury to intervening structures between the identified point on the pleural surface and the alternative point on the target location, based on the determined alternative access path, and displaying the access path and the calculated risk of injury for the access path on the 3D model further includes displaying alternative access path and the calculated risk of injury for the alternative access path on the 3D model.

In another aspect of the present disclosure, the method further includes providing an alert if the calculated risk of injury is more than a predetermined threshold.

In yet another aspect of the present disclosure, the access path is represented by a straight line.

In still another aspect of the present disclosure, the access path is represented by a curved line.

In yet another aspect of the present disclosure, the intervening structures are one or more of an airway wall, nerves, vascular lumens, vascular structures, lymphatic lumens, and lymphatic structures.

Provided in accordance with the present disclosure is a navigation planning and procedure system. In an aspect of the present disclosure, the system includes a display device, at least one processor in communication with the display, and a memory storing instructions that, when executed by the at least one processor, cause the at least one processor to generate a three-dimensional (3D) model of a patient's lungs, cause the display device to display the 3D model of the patient's lungs, select a target location in tissue of the patient's lungs as displayed on the 3D model, identify a point on a pleural surface of the patient's lungs with access to the target location, determine an access path between the target location and the point on the pleural surface, calculate a risk of injury to intervening structures between the identified point on the pleural surface and the target location, based on the determined access path, and cause the display device to display the access path and the calculated risk of injury for the access path on the 3D model.

In a further aspect of the present disclosure, the identified point on the pleural surface is a first identified point on the pleural surface and the access path is a first access path, and the memory further stores instructions which, when executed by the at least one processor, cause the at least one processor to identify a second point on the pleural surface with access to the target location, determine a second access path between the target location and the second identified point on the pleural surface, and calculate a risk of injury to intervening structures between the target location and the second identified point on the pleural surface, based on the determined second access path, displaying the first access path and the calculated risk of injury for the first access path on the 3D model further includes displaying the second access path and the calculated risk of injury for the second access path on the 3D model.

In yet a further aspect of the present disclosure, the memory further stores instructions which, when executed by the at least one processor, cause the at least one processor to determine which of the first and second access paths has a lower calculated risk of injury, and select the access path which is determined to have a lower risk of injury.

In another aspect of the present disclosure, the point on the pleural surface with access to the target location is identified based on input received from a user.

In a further aspect of the present disclosure, the memory further stores instructions which, when executed by the at least one processor, cause the at least one processor to identify an alternative point on the pleural surface with access to the target location, determine an alternative access path between the alternative point on the pleural surface and the target location, and calculate a risk of injury to intervening structures between the target location and the alternative point on the pleural surface, based on the determined alternative access path, and displaying the access path and the calculated risk of injury for the access path on the 3D model further includes displaying the alternative access path and the calculated risk of injury for the alternative access path on the 3D model.

In another aspect of the present disclosure, the memory further stores instructions which, when executed by the at least one processor, cause the at least one processor to receive a user input selecting a point on the target location as an end point for the access path, and the access path is determined between the identified point on the pleural surface and the point on the target location.

In yet another aspect of the present disclosure, the memory further stores instructions which, when executed by the at least one processor, cause the at least one processor to identify an alternative point on the target location as an alternative end point for the access path, determine an alternative access path between the identified point on the pleural surface and the alternative point on the target location, and calculate a risk of injury to intervening structures between the identified point on the pleural surface and the alternative point on the target location, based on the determined alternative access path, and displaying the access path and the calculated risk of injury for the access path on the 3D model further includes displaying alternative access path and the calculated risk of injury for the alternative access path on the 3D model.

Provided in accordance with the present disclosure is a non-transitory computer-readable storage medium storing instructions which, when executed by a processor, cause processor computer to generate a three-dimensional (3D) model of a patient's lungs, cause a display device to display the 3D model of the patient's lungs, select a target location in tissue of the patient's lungs as displayed on the 3D model, identify a point on a pleural surface of the patient's lungs with access to the target location, determine an access path between the target location and the identified point on the pleural surface, calculate a risk of injury to intervening structures between the target location and the point on the pleural surface, based on the determined access path, and cause a display device to display the access path and the calculated risk of injury for the access path on the 3D model.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION

Systems, devices, methods, and computer-readable media are provided for planning a procedure for the treatment of lung tissue, in accordance with the present disclosure. Generally, the lungs are imaged, using a CT imaging device, ultrasound, or other modality, and image data received from the imaging is used to generate a three-dimensional (3D) model of a of the patient's lungs. The 3D model may include various structures forming part of the patient's lungs, including luminal networks such as the bronchial network (also referred to herein as the airways), the vascular network, and the lymphatic network, as well as other structures including the pleura. Additionally, the image data is analyzed to identify various intervening structures, such as vasculature, lymphatic structures, organs including the heart and its associated structures, bone, cartilage, nerves, and the like, therein. The 3D model is displayed to a user as an image using a user interface, such as a display device. From the image, a starting point within an airway of the lung and an ending point at a target location are selected. An access path is generated between the starting point and the ending point, and a calculation is made as to a risk of injury that may occur if the tool is advanced along the access path. The calculation, or an indication showing the risk, may be displayed or otherwise provided to the user. In some embodiments, multiple starting points and multiple ending points are identified from the image, either by user selection or by interpolation, potential access paths are generated for each combination of starting point and ending point, and a risk of injury for each of the access paths is determined. In such configurations, an access path having the least risk of injury is identified and provided to the user.

By performing the above-described steps, the user may decide whether or not to include the access path in a patient's treatment plan. Additionally, the user may identify a preferred access path along which the tool may be advanced to thereby minimize injury to the patient during treatment. During performance of the treatment procedure, such as during navigation of surgical tools to a target location, as described further below, the risk of injury may continuously be recalculated and updated based on the position of the tools.

Figure 1:
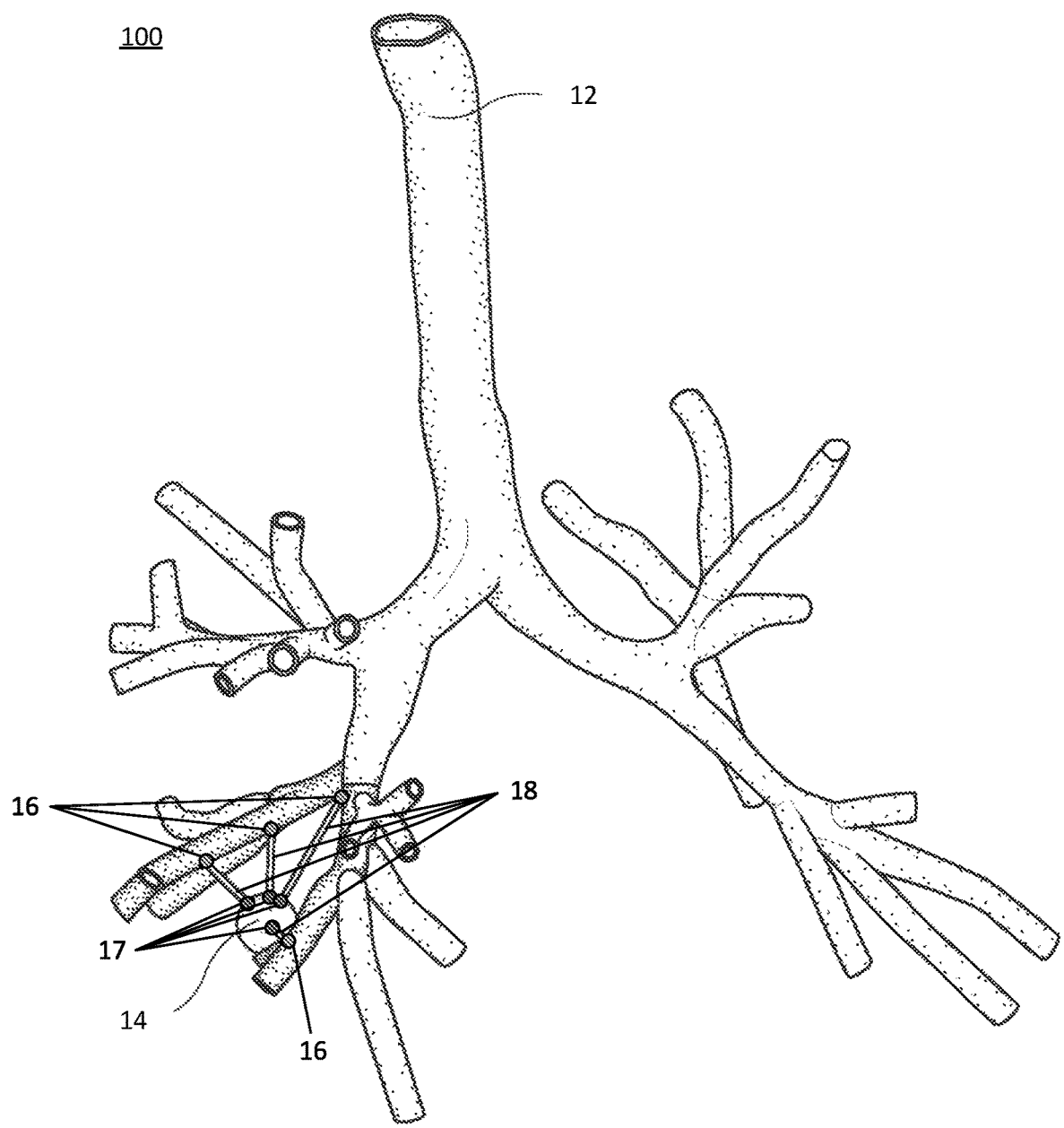
FIG. 1 shows an exemplary user interface for identifying access paths to a target location, according to an embodiment of the present disclosure.

An exemplary graphical user interface (GUI) 100 is shown in FIG. 1. GUI 100 may be used by the clinician to review access paths, as well as their corresponding start and end points. As shown in FIG. 1, GUI 100 may show a 3D model 12 and a target location 14, along with various access paths 18 connecting start points 16 on 3D model 12 with end points 17 on target location 14.

Figure 2:
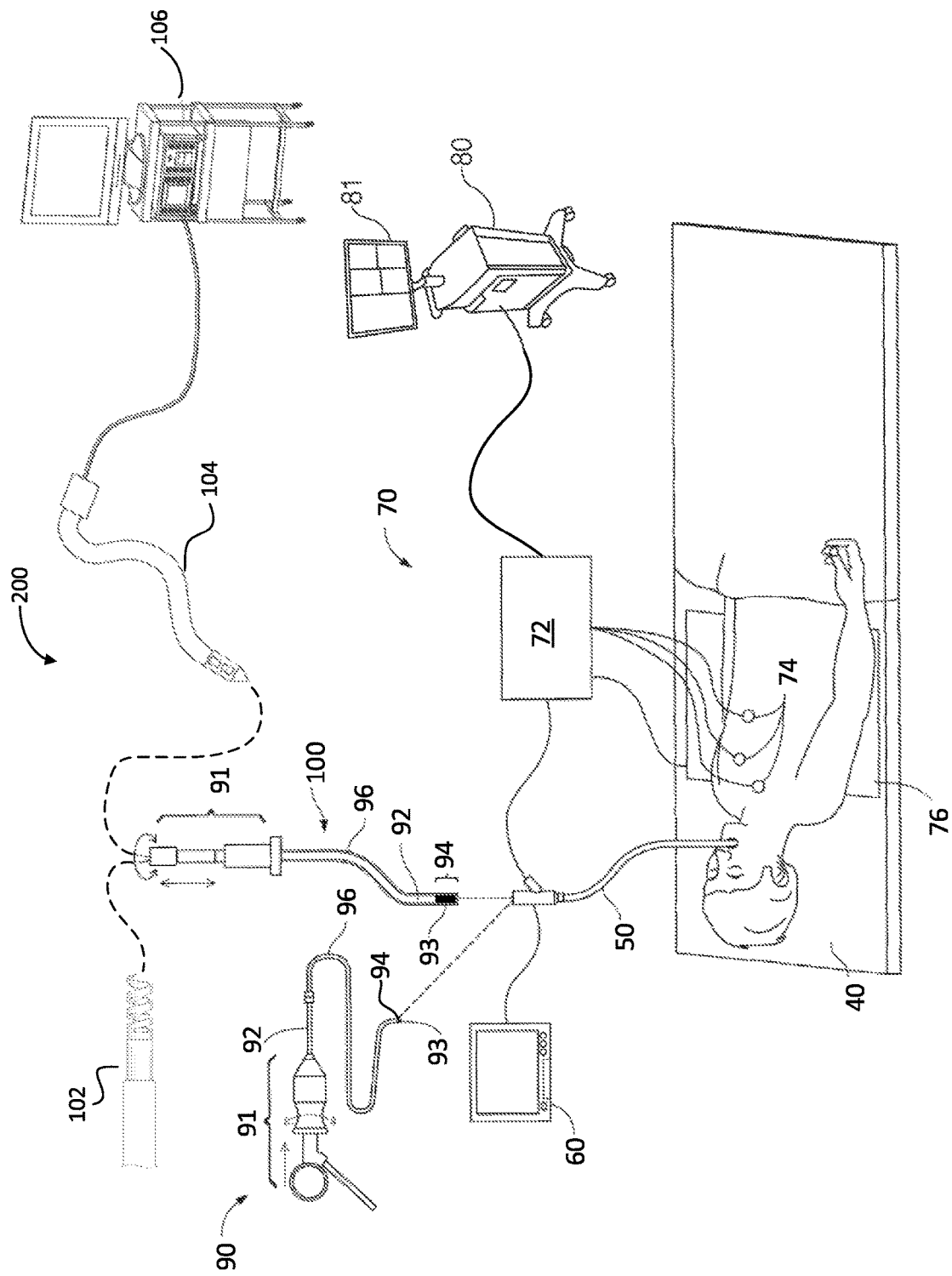
FIG. 2 is a system diagram of an electromagnetic navigation (EMN) system, according to an embodiment of the present disclosure.

With reference to FIG. 2, an electromagnetic navigation (EMN) system 200 is provided in accordance with an embodiment of the present disclosure. System 200 may be used to determine one or more pathways to target tissue, navigating a catheter guide assembly positioning assembly to the target tissue, navigate a treatment tool to the target tissue to perform treatment of the target tissue using the treatment tool, digitally mark the location where the treatment was performed, place one or more echogenic markers at or around the target tissue, among other things.

System 200 generally includes an operating table 40 configured to support a patient; a bronchoscope 50 configured for insertion through the patient's mouth and/or nose into the patient's airways; monitoring equipment 60 coupled to bronchoscope 50 for displaying video images received from bronchoscope 50; a tracking system 70 including a tracking module 72, a plurality of reference sensors 74, and an electromagnetic field generator 76; and a computing device 80 including software and/or hardware used to facilitate pathway planning, identification of target tissue, navigation to target tissue, and digitally marking the location of the target tissue.

FIG. 2 also depicts two types of catheter guide assemblies 90, 100. Both catheter guide assemblies 90, 100 are usable with system 200 and share a number of common components. Each catheter guide assembly 90, 100 includes a handle 91, which is connected to a navigation catheter, such as extended working channel (EWC) 96. EWC 96 is sized for placement into the working channel of a bronchoscope 50. In operation, a locatable guide (LG) 92, including an electromagnetic (EM) sensor 94, is inserted into EWC 96 and locked into position such that EM sensor 94 extends a desired distance beyond a distal tip 93 of EWC 96. The location of EM sensor 94, and thus the distal end of EWC 96, within an electromagnetic field generated by electromagnetic field generator 76 can be derived by tracking module 72, and computing device 80. Catheter guide assemblies 90, 100 have different operating mechanisms, but each contain a handle 91 that can be manipulated by rotation and compression to steer distal tip 93 of LG 92 and EWC 96. Catheter guide assemblies 90 are currently marketed and sold by Medtronic PLC under the name SUPERDIMENSION® Procedure Kits. Similarly, catheter guide assemblies 100 are currently sold by Medtronic PLC under the name EDGE™ Procedure Kits. Both kits include a handle 91, EWC 96, and LG 92. For a more detailed description of the catheter guide assemblies 90, 100, reference is made to commonly-owned U.S. Pat. No. 9,247,992 entitled MICROWAVE ABLATION CATHETER AND METHOD OF UTILIZING THE SAME, filed on Mar. 15, 2013, by Ladtkow et al., the entire contents of which are hereby incorporated by reference.

As illustrated in FIG. 2, the patient is shown lying on operating table 40 with bronchoscope 50 inserted through the patient's mouth and into the patient's airways. Bronchoscope 50 includes a source of illumination and a video imaging system (not explicitly shown) and is coupled to monitoring equipment 60, e.g., a video display, for displaying the video images received from the video imaging system of bronchoscope 50.

Catheter guide assemblies 90, 100 including LG 92 and EWC 96 are configured for insertion through a working channel of bronchoscope 50 into the patient's airways (although the catheter guide assemblies 90, 100 may alternatively be used without bronchoscope 50). LG 92 and EWC 96 are selectively lockable relative to one another via a locking mechanism 99. A six degrees-of-freedom electromagnetic tracking system 70, e.g., similar to those disclosed in commonly-owned U.S. Pat. No. 6,188,355, entitled WIRELESS SIX-DEGREE-OF-FREEDOM LOCATOR, filed on Dec. 14, 1998, by Gilboa, and published PCT Application Nos. WO 00/10456 and WO 01/67035, the entire contents of each of which are hereby incorporated by reference, or any other suitable positioning measuring system, is utilized for performing navigation, although other configurations are also contemplated. Tracking system 70 is configured for use with catheter guide assemblies 90, 100 to track the position of EM sensor 94 as it moves in conjunction with EWC 96 through the airways of the patient, as detailed below.

As shown in FIG. 2, EM field generator 76 is positioned beneath the patient. EM field generator 76 and the plurality of reference sensors 74 are interconnected with tracking module 72, which derives the location of each reference sensor 74 in six degrees of freedom. One or more of reference sensors 74 are attached to the chest of the patient. The six degrees of freedom coordinates of reference sensors 74 are sent to computing device 80, which includes an application 81 which uses data collected by sensors 74 to calculate a patient coordinate frame of reference.

Although EM sensor 94 is described above as being included in LG 92 it is also envisioned that EM sensor 94 may be embedded or incorporated within a biopsy tool 102 where biopsy tool 102 may alternatively be utilized for navigation without need of LG 92 or the necessary tool exchanges that use of LG 92 requires. Similarly, it is envisioned that EM sensor 94 may be embedded or incorporated within a microwave ablation tool 104, where microwave ablation tool 104 may alternatively be utilized for navigation without the need of LG 92 or the necessary tool exchanges that use of LG 92 requires.

During navigation, EM sensor 94, in conjunction with tracking system 70, enables tracking of EM sensor 94, and thereby LG 92 or a treatment tool, such as biopsy tool 102 and/or microwave ablation tool 104, as LG 92 or one of tools 102 and 104 is advanced through the patient's airways. As LG 92 or tools 102, and/or 104 is navigated to target location 14 within the patient, the sensed location of EM sensor 94 is displayed on the computing device 80 enabling the clinician to follow the pathway that was developed during the planning phase and reach a desired target for treatment. Following arrival at target location 14, the LG 92 may be removed allowing the insertion of one or more of tools 102 and/or 104.

Also shown in FIG. 2 is biopsy tool 102 that is insertable into catheter guide assemblies 90, 100 following navigation to a target and removal of LG 92. Biopsy tool 102 may be used to collect one or more tissue samples from target location 14 and in an embodiment, is further configured for use in conjunction with tracking system 70 to facilitate navigation of biopsy tool 102 to target location 14, and tracking of a location of biopsy tool 102 as it is manipulated relative to target location 14 to obtain the tissue sample. Similarly, microwave ablation tool 104 is configured to be insertable into catheter guide assemblies 90, 100 following navigation to target location 14 and removal of LG 92. Microwave ablation tool 104 is configured to be operated with a microwave generator 106, to treat tissue at target location 14 by, for example, using microwave energy to heat and denature proteins in the tissue resulting in coagulation and death of specific tissue. Microwave ablation tool 104 may include any of a variety of microwave ablation tools and/or catheters, examples of which are more fully described in commonly-owned U.S. Pat. Nos. 9,259,269; 9,247,993; and 9,044,254; and co-pending U.S. Patent Application Publication Nos. 2014/0046176 and 2014/0046211, all entitled "MICROWAVE ABLATION CATHETER AND METHOD OF USING THE SAME", filed on Mar. 15, 2013, by Ladtkow et al., the entire contents of each of which are hereby incorporated by reference. Though shown as a biopsy tool 102 and microwave ablation tool 104 in FIG. 2, those of skill in the art will recognize that other tools, including, for example RF ablation tools, chemotherapy tools, cryoablation tools, and others may be similarly deployed and tracked without departing from the scope of the present disclosure.

Figure 3:
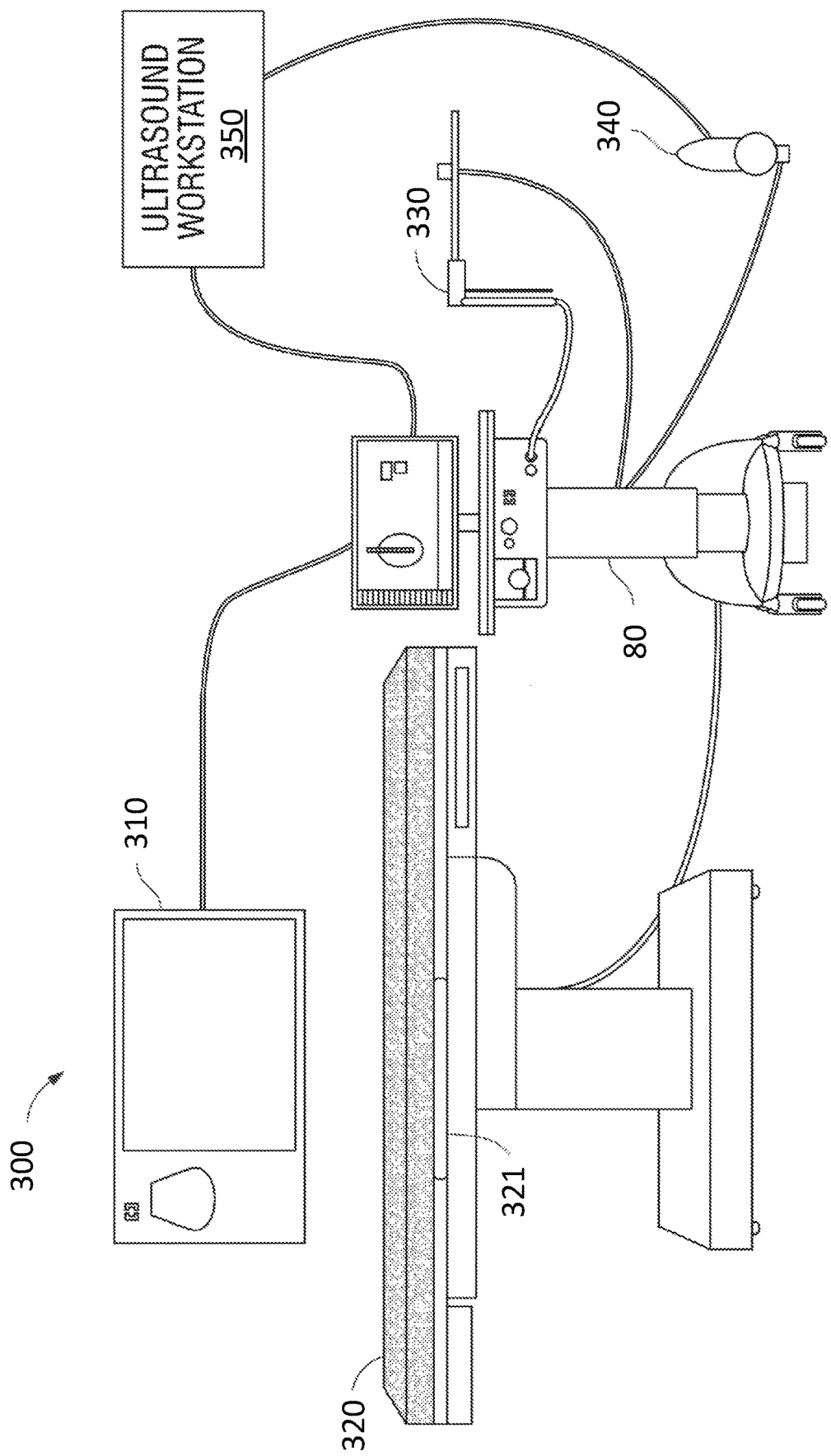
FIG. 3 is a schematic diagram of a microwave ablation planning and procedure system according to an embodiment of the present disclosure.

In another embodiment, the features of the present disclosure may also be used in a percutaneous treatment system. As such, FIG. 3 illustrates an exemplary treatment system 300, which includes a computing device 80, a display 310, a table 320, a treatment tool 330, and an ultrasound sensor 340 connected to an ultrasound workstation 350. Similar to the computing device described above with reference to FIG. 2, computing device 80 may be, for example, a laptop computer, desktop computer, tablet computer, or other similar device. Computing device 80 may be configured to control an electrosurgical generator, a peristaltic pump, a power supply, and/or any other accessories and peripheral devices relating to, or forming part of, system 300. Display 310 is configured to output instructions, images, and messages relating to the performance of the treatment procedure. Table 320 may be, for example, an operating table or other table suitable for use during a treatment procedure, which includes an electromagnetic (EM) field generator 321. EM field generator 321 is used to generate an EM field during the treatment procedure and forms part of an EM tracking system that is used to track the positions of surgical instruments within the body of a patient. EM field generator 321 may include various components, such as a specially designed pad to be placed under, or integrated into, an operating table or patient bed. An example of such an EM tracking system is the AURORA™ system sold by Northern Digital Inc. Treatment tool 330 is a surgical instrument for percutaneously accessing and treating a target location. For example, treatment tool 330 may be an ablation probe having a microwave ablation antenna that is used to ablate tissue. While the present disclosure describes the use of system 300 in a surgical environment, it is also envisioned that some or all of the components of system 300 may be used in alternative settings, for example, an imaging laboratory and/or an office setting.

In addition to the EM tracking system, the surgical instruments may also be visualized by using ultrasound imaging. Ultrasound sensor 340, such as an ultrasound wand, may be used to image the patient's body during the treatment procedure to visualize the location of the surgical instruments, such as treatment tool 330, inside the patient's body. Ultrasound sensor 340 may have an EM tracking sensor embedded within or attached to the ultrasound wand, for example, a clip-on sensor or a sticker sensor. As described further below, ultrasound sensor 340 may be positioned in relation to treatment tool 330 such that treatment tool 330 is at an angle to the ultrasound image plane, thereby enabling the clinician to visualize the spatial relationship of treatment tool 330 with the ultrasound image plane and with objects being imaged. Further, the EM tracking system may also track the location of ultrasound sensor 340. In some embodiments, one or more ultrasound sensors 340 may be placed inside the body of the patient. EM tracking system may then track the location of such ultrasound sensors 340 and treatment tool 330 inside the body of the patient. Ultrasound workstation 350 may be used to configure, operate, and view images captured by ultrasound sensor 340.

Various other surgical instruments or surgical tools, such as LigaSure™ devices, surgical staples, etc., may also be used during the performance of a treatment procedure. In embodiment where treatment tool 330 is an ablation probe, the ablation probe is used to ablate a lesion or tumor (hereinafter referred to as a "target") by using electromagnetic radiation or microwave energy to heat tissue in order to denature or kill cancerous cells. The construction and use of a system including such an ablation probe is more fully described in commonly-owned co-pending U.S. Patent Publication No. 2016/0058507, entitled MICROWAVE ABLATION SYSTEM, filed on Aug. 26, 2014, by Dickhans, U.S. Pat. No. 9,247,992 by Latkow et al., described above, and commonly-owned U.S. Pat. No. 9,119,650, entitled MICROWAVE ENERGY-DELIVERY DEVICE AND SYSTEM, filed on Mar. 15, 2013, by Brannan et al., the contents of all of which is hereby incorporated by reference in its entirety.

The location of treatment tool 330 within the body of the patient may be tracked during the treatment procedure. An example method of tracking the location of treatment tool 330 is by using the EM tracking system, which tracks the location of treatment tool 330 by tracking sensors attached to or incorporated in treatment tool 330. Various types of sensors may be used, such as a printed sensor, the construction and use of which is more fully described in commonly-owned co-pending U.S. patent application Ser. No. 14/919, 950, entitled "MEDICAL INSTRUMENT WITH SENSOR FOR USE IN A SYSTEM AND METHOD FOR ELEC- TROMAGNETIC NAVIGATION", filed Oct. 22, 2015, by Greenburg et al., the entire contents of which is incorporated herein by reference. A percutaneous treatment system similar to the above-described system 300 is further described in commonly-owned co-pending U.S. patent application Ser. Nos. 15/099,698, 15/099,730, 15/099,772, 15/099,820, and 15/099,665, all filed on Apr. 15, 2016, by Girotto et al., the entire contents of each of which is incorporated herein by reference.

Figure 4A:
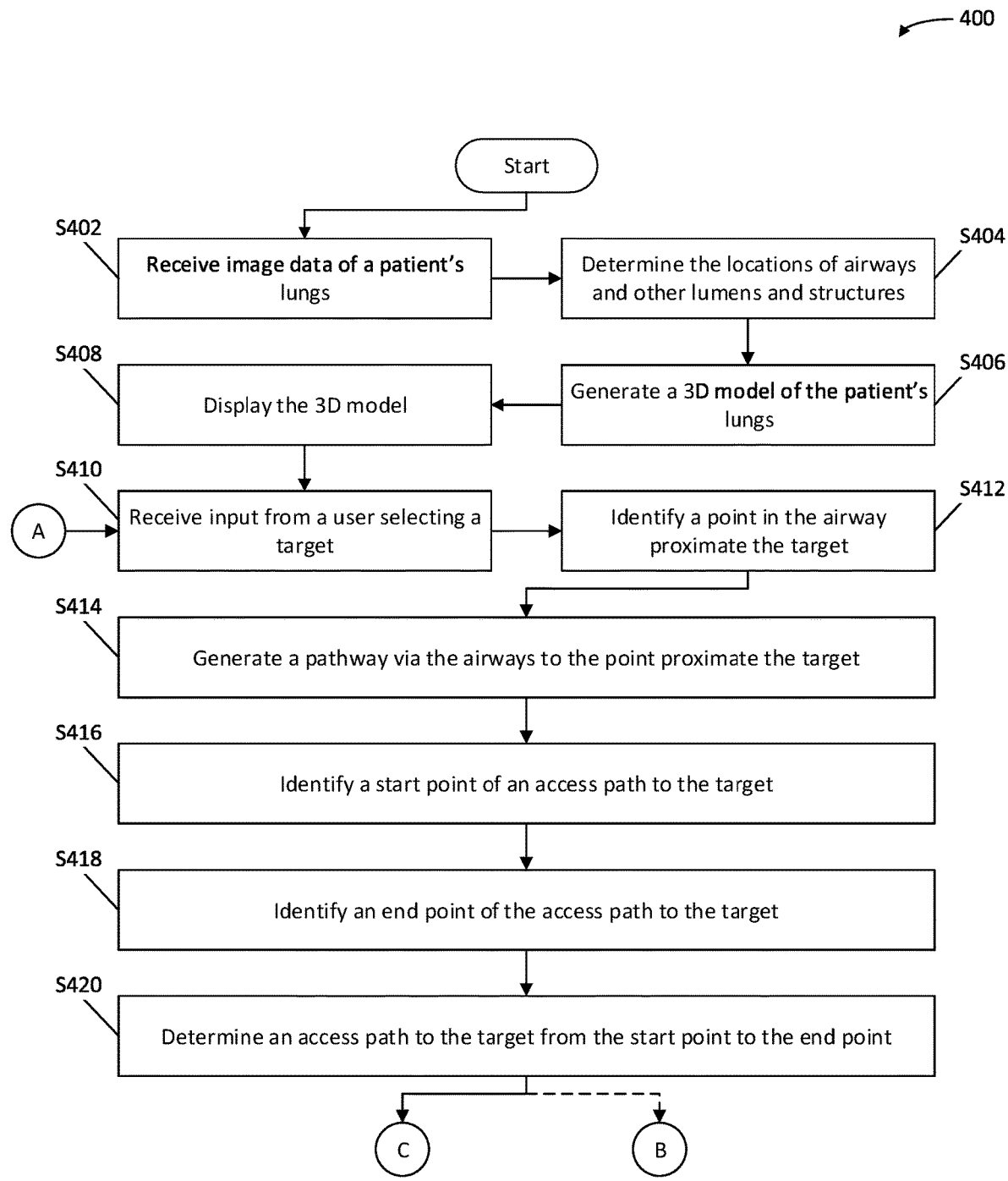
FIGS. 4A and 4B is a flow diagram of a method for planning a procedure for treatment of lung tissue, according to an embodiment of the present disclosure.
Figure 4B:
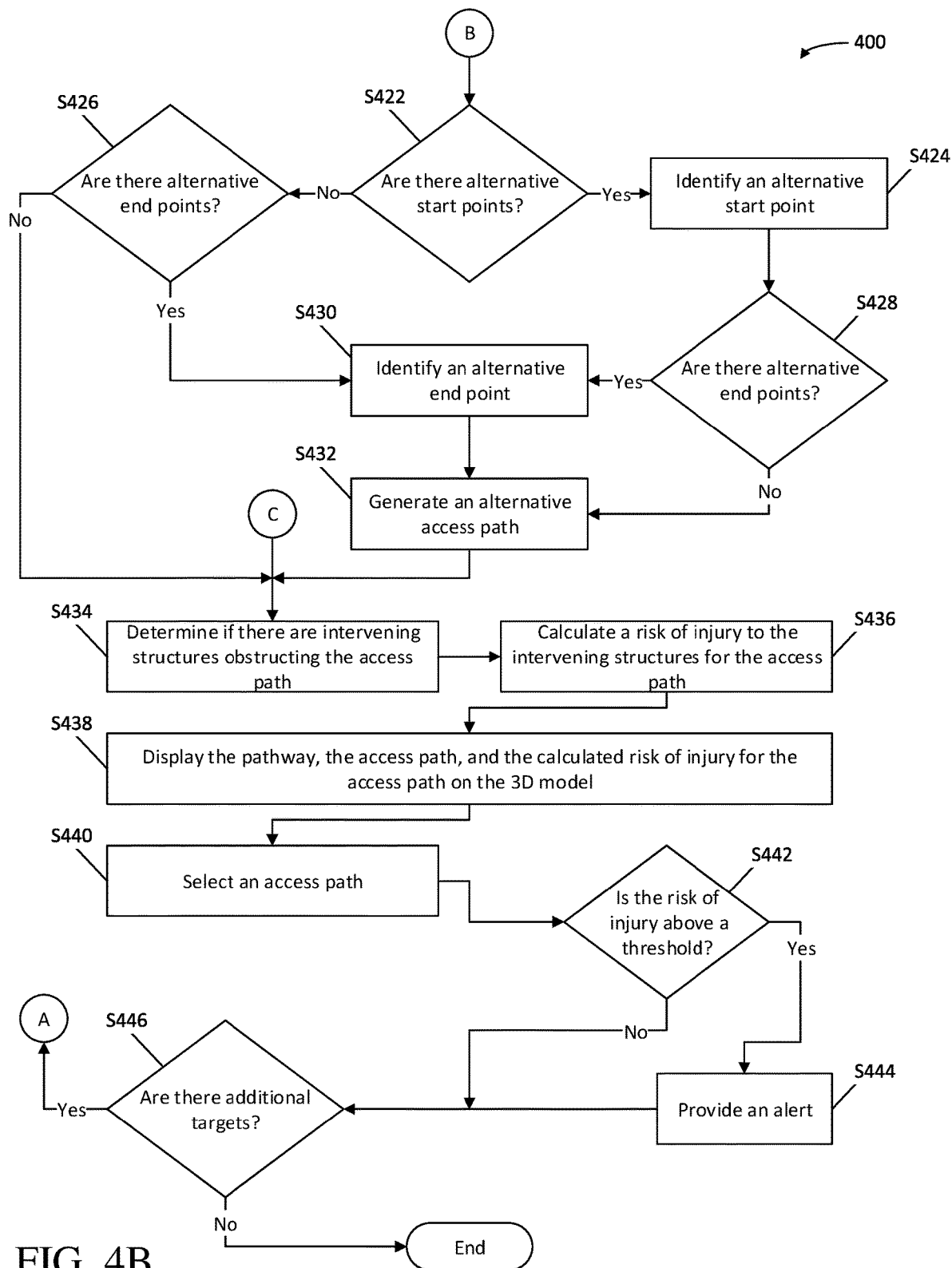

To minimize the risk of injury to tissue when using the treatment tools, for example tools 102, 104, 330, during a treatment procedure, planning is performed prior to the treatment procedure. For example, as noted briefly above, access paths 18 are generated between selected starting points and selected ending points, and calculations are made as to the risk of injury that may occur, if the tool is advanced along access paths 18. In this regard, turning now to FIGS. 4A and 4B, there is shown a flow diagram of a method 400 for planning a procedure for treatment of lung tissue, according to an embodiment of the present disclosure. While the description of method 400 provided below uses an example embodiment where the patient's airways are used as an access route to the target location, those skilled in the art will recognize that other luminal networks, such as the vascular network, the lymphatic network, the gastrointestinal network, the genitourinary tract, etc., may also be used without departing from the scope of the present disclosure.

Starting at step S402, computing device 80 receives image data of a patient's lungs. The image data may be assembled by using, for example, CT imaging, magnetic resonance imaging (MRI), ultrasound, cone beam CT (CBCT), X-ray imaging, and/or any other relevant imaging modality known to those skilled in the art. The image data may be provided in, for example, the digital imaging and communications in medicine (DICOM) standard or another appropriate imaging format or standard known to those skilled in the art.

Next, at step S404, application 81, executing on computing device 80, analyzes the image data to determine locations of airways and other lumens and structures. The other lumens and structures may include vascular lumens and structures, lymphatic lumens and structures, the pleura of the lungs, bones, cartilage, nerves, organs, implanted devices, and/or any other relevant objects detectable in the image data. Application 81 may use various image analysis and image processing techniques, including region growing techniques to determine the locations of the airways and other lumens and structures in the image data. Examples of systems, devices, and methods for using such image processing and region growing techniques are disclosed in commonly-owned co-pending U.S. Patent Publication No. 2016/0038248, entitled "TREATMENT PROCEDURE PLANNING SYSTEM AND METHOD", filed on Aug. 10, 2015, by Bharadwaj et al., and commonly-owned co-pending U.S. Patent Publication No. 2016/0005193, entitled "SYSTEM AND METHOD FOR SEGMENTATION OF LUNG", filed on Jun. 30, 2015, by Markov et al., the entire contents of each of which are incorporated herein by reference. In addition, application 81 may use data regarding the movement of the patient's airways during the patient's respiratory cycle to compensate for differences in the detected locations of the patient's airway, vascular, and/or lymphatic networks. Systems, devices, and methods for detecting movement of the patient's airways during the patient's respiratory cycle are further described in commonly-owned co-pending U.S. Patent Application Publication No. 2009/0156951, entitled "PATIENT BREATHING MODELING", filed on Jul. 9, 2008, by Dorian Averbuch, and commonly-owned U.S. Pat. No. 7,233,820, entitled "ENDOSCOPE STRUCTURES AND TECHNIQUES FOR NAVIGATING TO A TARGET IN BRANCHED STRUCTURE", filed on Apr. 16, 2003, by Pinhas Gilboa, the entire contents of both of which are incorporated herein by reference.

Thereafter, at step S406, application 81 generates a three-dimensional (3D) model 12 of the patient's lungs. 3D model 12 may be based on the determined locations of the patient's airways, and may also show any or all of the other lumens and structures described above.

At step S408, application 81 may cause a display device, such as display 706 (FIG. 7) of computing device 80, described below, to display 3D model 12. A user, such as a surgeon, technician, and/or any other appropriate clinician (referred to herein collectively as "clinician") may examine 3D model 12 of the patient's lungs and the various lumens and structures depicted therein to identify one or more target locations where treatment may be performed. The clinician may provide, via for example input device 710 (FIG. 7) of computing device 80, described below, user input selecting a target location, and application 81 may receive the input selecting target location 14 at step S410. Alternatively, or in addition, application 81 may process the image data and may identify one or more target locations automatically, such as via computer-aided diagnosis (CAD) methods.

Next, application 81 may, at step S412, identify a point in an airway proximate to or at target location 14 to where a treatment tool, such as biopsy tool 102, microwave ablation tool 106, and/or any other appropriate treatment tools may be navigated. For example, the point in the airway proximate to or at target location 14 may be a point in the airways that is closest to target location 14 selected at step S410. Alternatively, the point in the airway proximate to or at target location 14 may be a point in the airways from which target location 14 may be most easily accessed.

Thereafter, at step S414, application 81 generates a pathway from the patient's trachea via the patient's airways to the point proximate to or at target location 14. Alternatively, the pathway may be generated starting at the point proximate to or at target location 14 and reaching back through the patient's airways to the patient's trachea. In some embodiments, multiple pathways may be generated for approach to a single target. These pathways may each be associated with an access path 18 as described hereinbelow.

At step S416, a start point 16 of an access path 18 to target location 14 is identified. Start point 16 is a location on the airway wall at which tools or treatment devices will exit the airway in order to reach target location 14. Access path 18 is a pathway from this start point to target location 14. In an embodiment, application 81 may receive an input identifying start point 16 of access path 18 to target location 14. For example, the clinician may view 3D model 12 and use input device 710 of computing device 80, described below, to identify the point proximate to or at target location 14 to which the pathway was generated as start point 16 of access path 18 to target location 14. Alternatively, the clinician may select another point along the airways as start point 16 of access path 18 to target location 14. As shown in FIG. 1 (described above), various start points may be identified and/or selected. For example, the clinician may select another point along the airways based on the physiology of the patient, e.g., to avoid large blood vessels or lymphatic structures, and/or to ensure an easier access path 18 for tools to be manipulated along to reach target location 14. In another embodiment, application 81 may select start point 16 without receiving input from the clinician. For example, application 81 may automatically identify the point proximate to or at target location 14 to which the pathway was generated as start point 16 of access path 18 to target location 14. Alternatively, application 81 may automatically select another point along the airways as start point 16 of access path 18 to target location 14. For example, application 81 may identify start point 16 based on the local physiology of the patient's airways and target location 14, e.g., the curvature of the airways, the distance between target location 14 and the airways, etc.

Similarly, at step S418, an end point 17 of access path 18 to target location 14 may be identified. In an embodiment, application 81 may receive input identifying end point 17 of access path 18 to target location 14. For example, the clinician may view 3D model 12 and use input device 410 of computing device 80, described below, to select as end point 17 a point on target location 14 closest to the identified start point. Alternatively, the clinician may select any other point on target location 14 as end point 17, such as a point providing the easiest access from the airways and/or the point on target location 14 providing the best access or that is closest to the airways. In another embodiment, application 81 may select end point 17 without receiving input from the clinician. For example, application 81 may automatically identify the point on the target closest to the identified start point as end point 17 of access path 18 to target location 14. Alternatively, application 81 may automatically select any other point on target location 14 as end point 17 of access path 18 to target location 14. For example, application 81 may identify end point 17 based on the local physiology of the patient's airways and target location 14, e.g., the curvature of the airways, the distance between target location 14 and the airways, etc. In addition, the structure of the tool or medical device may be a factor in determining end point 17. In some instances, it may be desirable to pass the medical device or tool completely through the center of target location 14, and beyond the distal edge of target location 14. In such instances, end point 17 may be on the opposite side of target location 14 and outside of target location 14 as compared to start point 16. As an example, some microwave ablation devices are structured such that their ablation zone is proximal of the distal tip of the microwave ablation device, and thus the distal tip may need to be placed outside target location 14 for maximum efficiency and treatment effects. In another example, a treatment site, which is an area that includes target location 14 and a margin area, e.g., an area extending a short distance around target location 14, may be included as a factor for selecting end point 17 of access path 18 such as to ensure that, depending on the type of treatment to be applied to target location 14, the entire target location 14 will be treated.

In an embodiment, the clinician may provide multiple start points and/or end points as potential start and/or end points for an access path to target location 14, and allow application 81 to determine which combination of start and end points provides the best access path to target location 14, as described further below. In another embodiment, the clinician may not provide any start or end points, or may provide only start points and no end points, or only end points and no start points. In any case, application 81 determines appropriate start and/or end points for access path 18 to target location 14.

At step S420, application 81 determines an access path to target location 14, based on either one or more of the clinician-selected start and end points, or based on the automatically selected start and end point. For example, application 81 may determine an access path based on a first combination of start and end points provided by the clinician. This may be repeated until an access path is determined for every combination of start and end points provided by the clinician. In some instances, it will be desirable to have multiple access paths to a target to ensure complete treatment or biopsy sampling. Further, by pre-defining multiple access paths, should the clinician experience an issue with one of the access paths 18, alternative approaches are already defined for the clinician, thus erasing the time and effort necessary to commence an alternative approach.

Alternatively or additionally, application 81 may also automatically determine start and/or end points, as described above, and use the automatically determined start and/or end points to determine an access path to target location 14.

After step S420 is completed, the method may include alternative approaches. In at least one embodiment, following path B, application 81 may display a prompt to the user asking whether additional or alternative start and/or end points should be determined. If the user does not want additional or alternative start and/or end points to be determined, the method may proceed to step S434. However, if the user wants additional or alternative start and/or end points to be determined, the method may proceed via an optional branch to step S422, where application 81 determines whether there are alternative start points to those provided by the clinician. If there are alternative start points, the method proceeds to step S424, where application 81 identifies one or more alternative start points. However, if it is determined that there are no alternative start points, the method proceeds to step S426, where application 81 determines if there are alternative end points. If it is determined that there are no alternative end points, the method skips to step S434.

After an alternative start point is identified at step S424, the method proceeds to step S428, where a determination similar to step S426 is made as to whether there are alternative end points. Thus, if at either step S426 or S428 application 81 determines that there are alternative end points, the method proceeds to step S430, where application 81 identifies one or more alternative end points. After an alternative end point is identified, or if it is determined at step S428 that there are no alternative end points, the method proceeds to step S432 where application 81 generates an alternative access path based on one of the alternative start points identified at step S424 and/or one of the alternative end points identified at step S430. This may be repeated until an access path is determined for every combination of start and end points determined at steps S424 and S430, as well as the start and end points provided by the clinician.

Thereafter, or in instances where no alternative start and end points are desired, the method may skip to path C, and initiate step S434, where application 81 determines whether there are intervening structures obstructing any of the access paths 18 determined at step S420 or any of the alternative access paths determined at step S432. For example, application 81 may determine whether there are other airways, vascular and/or lymphatic structures or lumens or any of the other structures detected at step S404 obstructing any of the access paths 18. Additionally, application 81 may determine whether there are any such intervening structures that may not be obstructing an access path but are still in close proximity to an access path to create a risk of injury.

Next, at step S436, application 81 calculates a risk of injury to the intervening structures based on access path 18. The risk of injury may be based on the local physiology of the patient's lungs, i.e. the intervening structures detected at step S434, as well as the type of tissue through which access path 18 runs and the type of tools to be used. For example, the closer the proximity of an intervening structure to access path 18, the higher the risk of injury calculated for that access path. Similarly, while it is inherent that there will be some tissue damage regardless, damage to blood vessels greater than a certain size or certain types of tissue may want to be clearly avoided. Additionally, certain tools may be more or less likely to damage certain types of tissue.

This process may be repeated until a risk of injury is calculated for each access path and alternative access path. Additionally, as noted above, the risk of injury may subsequently be recalculated and updated during navigation of tools 102, 104, 330 inside the patient's airways based on the detected location of EM sensor 94. A risk of injury may also be calculated for the treatment procedure itself, e.g. a biopsy, based on the selected access path 18 and end point 17 on target location 14. For example, application 81 may calculate a risk of injury for a biopsy based on the vasculature and tissue surrounding and interposed within target location 14. Such risk of injury for the treatment procedure may be combined with the risk of injury calculated for the access paths 18 and/or be maintained as a separate risk of injury.

Thereafter, at step S438, application 81 causes the display device to display the pathway generated at step S414, the access paths 18 determined at step S420, the alternative access paths determined at step S432, and the calculated risk of injury for each access path and alternative access path, on 3D model 12. The risk of injury may be displayed as a numerical value, such as a percentage or probability ratio, and/or as a graphical indicator, such as having the color in which access path 18 is displayed change according to the calculated risk for that access path. In an embodiment, the access paths 18 may be prioritized based on their associated risk of injury, and displayed to the user in order of their associated risk of injury. The risk of injury to target location 14 may also be displayed as combined with and/or separate from the risk of injury calculated for access path 18.

The clinician may review the displayed access paths and their associated risk of injury, and may select, at step S440, a preferred access path to be used during the treatment procedure. Alternatively, application 81 may determine which access path has the lowest risk of injury, and may pre-select that access path for the clinician's review and approval.

After an access path is selected, application 81 determines, at step S442, whether the risk of injury calculated for that access path is above a predetermined threshold. If the risk of injury is determined to be above the predetermined threshold, the method proceeds to step S424, where an alert is provided. The alert may be a graphical alert displayed on the display device, and/or an audible alert emitted by computing device 80. In some embodiments the clinician may be required to acknowledge the alert regarding the risk and effectively accept the risk.

Thereafter, or if it is determined that the risk of injury is not above the predetermined threshold, the method proceeds to step S446 where a determination is made if there are additional target locations for which access paths have to be determined. If there are additional target locations, the method returns to step S410. If there are no additional target locations, the method ends.

Figure 5A:
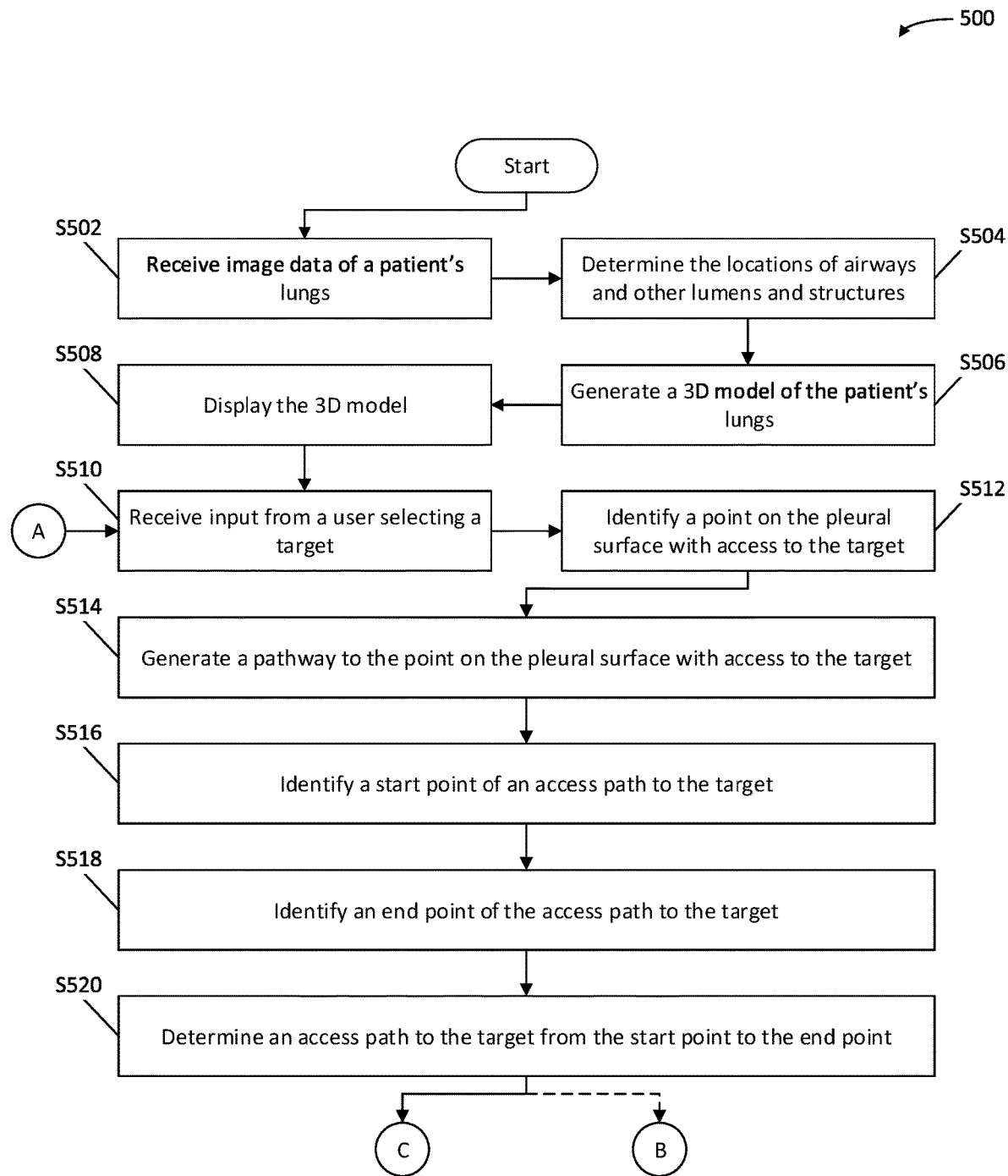
FIGS. 5A and 5B is a flow diagram of a method for planning a procedure for treatment of lung tissue via percutaneous access to the lungs, according to an embodiment of the present disclosure.
Figure 5B:
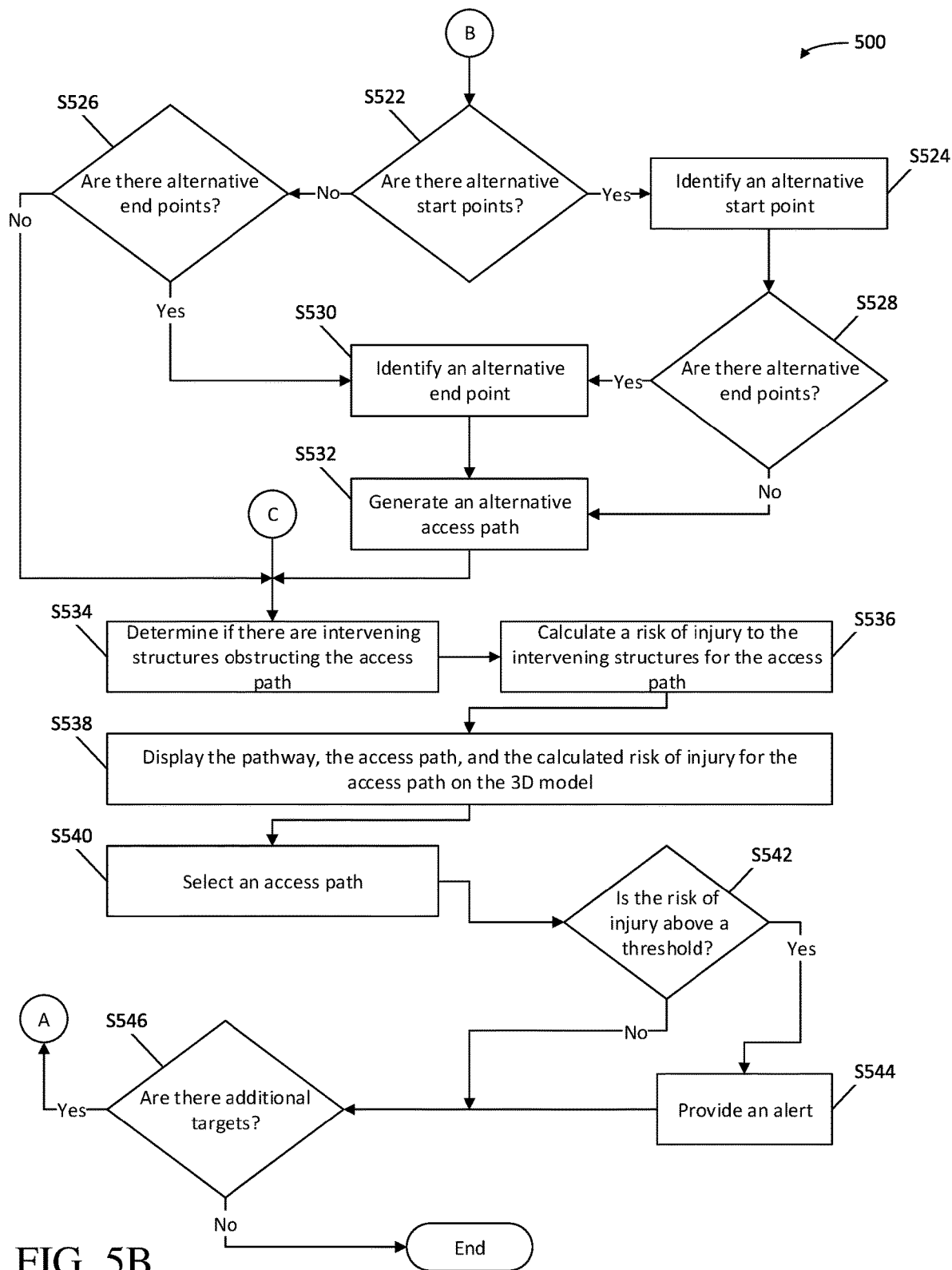

In addition to the above-described method of accessing the target location via bronchial navigation within the patient's airways, the target location may also be accessed percutaneously by using a system such as system 300, described above with reference to FIG. 3. In that regard, turning now to FIGS. 5A and 5B, there is shown a flow diagram of a method 500 for planning a procedure for treatment of lung tissue via percutaneous access to the lungs, according to an embodiment of the present disclosure.

Starting at step S502, computing device 80 receives image data of a patient's lungs. The image data may be assembled by using, for example, CT imaging, magnetic resonance imaging (MRI), ultrasound, cone beam CT (CBCT), X-ray imaging, and/or any other relevant imaging modality known to those skilled in the art. The image data may be provided in, for example, the digital imaging and communications in medicine (DICOM) standard or another appropriate imaging format or standard known to those skilled in the art.

Next, at step S504, application 81, executing on computing device 80, analyzes the image data to determine locations of airways and other lumens and structures. The other lumens and structures may include vascular lumens and structures, lymphatic lumens and structures, the pleura of the lungs, bones, cartilage, nerves, organs, implanted devices, and/or any other relevant objects detectable in the image data. Application 81 may use various image analysis and image processing techniques, including region growing techniques to determine the locations of the airways and other lumens and structures in the image data. Examples of systems, devices, and methods for using such image processing and region growing techniques are described above with reference to FIG. 4A. In addition, application 81 may use data regarding the movement of the patient's airways during the patient's respiratory cycle to compensate for differences in the detected locations of the patient's airway, vascular, and/or lymphatic networks. Systems, devices, and methods for detecting movement of the patient's airways during the patient's respiratory cycle is also described above with reference to FIG. 4A.

Thereafter, at step S506, application 81 generates a three-dimensional (3D) model 12 of the patient's lungs. 3D model 12 may be based on the determined locations of the patient's airways, and may also show any or all of the other lumens and structures described above.

At step S508, application 81 may cause a display device, such as display 706 (FIG. 7) of computing device 80, described below, to display 3D model 12. A user, such as a surgeon, technician, and/or any other appropriate clinician (referred to herein collectively as "clinician") may examine 3D model 12 of the patient's lungs and the various lumens and structures depicted therein to identify one or more target locations where treatment may be performed. The clinician may provide, via for example input device 710 (FIG. 7) of computing device 80, described below, user input selecting a target location, and application 81 may receive the input selecting target location 14 at step S510. Alternatively, or in addition, application 81 may process the image data and may identify one or more target locations automatically, such as via computer-aided diagnosis (CAD) methods.

Next, application 81 may, at step S512, identify a point on a pleural surface with access to target location 14 to where a treatment tool, such as treatment tool 330 and/or any other appropriate treatment tools may be navigated. For example, the point on the pleural surface with access to target location 14 may be a point on the pleural surface that is closest to target location 14 selected at step S510. Alternatively, the point on the pleural surface with access to target location 14 may be a point on the pleural surface from which target location 14 may be most easily accessed.

Thereafter, at step S514, application 81 generates a pathway from a percutaneous entry point to the point on the pleural surface with access to target location 14. Alternatively, the pathway may be generated starting at the point on the pleural surface with access to target location 14 and reaching back to the percutaneous entry point. In some embodiments, multiple pathways may be generated for approach to a single target. These pathways may each be associated with an access path 18 as described hereinbelow. Systems, devices, and methods for generating a percutaneous pathway to a treatment location is further described in commonly-owned co-pending U.S. Patent Publication No. 2016/0038247, entitled "TREATMENT PROCEDURE PLANNING SYSTEM AND METHOD", filed on Aug. 10, 2015, by Bharadwaj et al., the entire contents of which are incorporated herein by reference.

At step S516, a start point 16 of an access path 18 to target location 14 is identified. Start point 16 is a location on the pleural surface at which tools or treatment devices will enter the patient's lungs in order to reach target location 14. Access path 18 is a pathway from this start point to target location 14. In an embodiment, application 81 may receive an input identifying start point 16 of access path 18 to target location 14. For example, the clinician may view 3D model 12 and use input device 710 of computing device 80, described below, to identify the point on the pleural surface with access to target location 14 to which the pathway was generated as start point 16 of access path 18 to target location 14. Alternatively, the clinician may select another point on the pleural surface as start point 16 of access path 18 to target location 14. As shown in FIG. 1 (described above), various start points may be identified and/or selected. For example, the clinician may select another point on the pleural surface based on the physiology of the patient, e.g., to avoid large blood vessels or lymphatic structures, and/or to ensure an easier access path 18 for tools to be manipulated along to reach target location 14. In another embodiment, application 81 may select start point 16 without receiving input from the clinician. For example, application 81 may automatically identify the point on the pleural surface with access to target location 14 to which the pathway was generated as start point 16 of access path 18 to target location 14. Alternatively, application 81 may automatically select another point on the pleural surface as start point 16 of access path 18 to target location 14. For example, application 81 may identify start point 16 based on the local physiology of the patient's lungs and target location 14, e.g., the locations of airways, vascular structures, the distance between target location 14 and the pleural surface, etc.

Similarly, at step S518, an end point 17 of access path 18 to target location 14 may be identified. In an embodiment, application 81 may receive input identifying end point 17 of access path 18 to target location 14. For example, the clinician may view 3D model 12 and use input device 410 of computing device 80, described below, to select as end point 17 a point on target location 14 closest to the identified start point. Alternatively, the clinician may select any other point on target location 14 as end point 17, such as a point providing the easiest access from the pleural surface and/or the point on target location 14 providing the best access or that is closest to the pleural surface. In another embodiment, application 81 may select end point 17 without receiving input from the clinician. For example, application 81 may automatically identify the point on the target closest to the identified start point as end point 17 of access path 18 to target location 14. Alternatively, application 81 may automatically select any other point on target location 14 as end point 17 of access path 18 to target location 14. For example, application 81 may identify end point 17 based on the local physiology of the patient's lungs and target location 14, e.g., the curvature of the airways and vascular lumens, the distance between target location 14 and the airways, etc. In addition, the structure of the tool or medical device may be a factor in determining end point 17. In some instances, it may be desirable to pass the medical device or tool completely through the center of target location 14, and beyond the distal edge of target location 14. In such instances, end point 17 may be on the opposite side of target location 14 and outside of target location 14 as compared to start point 16. As an example, some microwave ablation devices are structured such that their ablation zone is proximal of the distal tip of the microwave ablation device, and thus the distal tip may need to be placed outside target location 14 for maximum efficiency and treatment effects. In another example, a treatment site, which is an area that includes target location 14 and a margin area, e.g., an area extending a short distance around target location 14, may be included as a factor for selecting end point 17 of access path 18 such as to ensure that, depending on the type of treatment to be applied to target location 14, the entire target location 14 will be treated.

In an embodiment, the clinician may provide multiple start points and/or end points as potential start and/or end points for an access path to target location 14, and allow application 81 to determine which combination of start and end points provides the best access path to target location 14, as described further below. In another embodiment, the clinician may not provide any start or end points, or may provide only start points and no end points, or only end points and no start points. In any case, application 81 determines appropriate start and/or end points for access path 18 to target location 14.

At step S520, application 81 determines an access path to target location 14, based on either one or more of the clinician-selected start and end points, or based on the automatically selected start and end point. For example, application 81 may determine an access path based on a first combination of start and end points provided by the clinician. This may be repeated until an access path is determined for every combination of start and end points provided by the clinician. In some instances, it will be desirable to have multiple access paths to a target to ensure complete treatment or biopsy sampling. Further, by pre-defining multiple access paths, should the clinician experience an issue with one of the access paths 18, alternative approaches are already defined for the clinician, thus erasing the time and effort necessary to commence an alternative approach.

Alternatively or additionally, application 81 may also automatically determine start and/or end points, as described above, and use the automatically determined start and/or end points to determine an access path to target location 14.

After step S520 is completed, the method may include alternative approaches. In at least one embodiment, following path B, application 81 may display a prompt to the user asking whether additional or alternative start and/or end points should be determined. If the user does not want additional or alternative start and/or end points to be determined, the method may proceed to step S534. However, if the user wants additional or alternative start and/or end points to be determined, the method may proceed via an optional branch to step S522, where application 81 determines whether there are alternative start points to those provided by the clinician. If there are alternative start points, the method proceeds to step S524, where application 81 identifies one or more alternative start points. However, if it is determined that there are no alternative start points, the method proceeds to step S526, where application 81 determines if there are alternative end points. If it is determined that there are no alternative end points, the method skips to step S534.

After an alternative start point is identified at step S524, the method proceeds to step S528, where a determination similar to step S526 is made as to whether there are alternative end points. Thus, if at either step S526 or S528 application 81 determines that there are alternative end points, the method proceeds to step S530, where application 81 identifies one or more alternative end points. After an alternative end point is identified, or if it is determined at step S528 that there are no alternative end points, the method proceeds to step S532 where application 81 generates an alternative access path based on one of the alternative start points identified at step S524 and/or one of the alternative end points identified at step S530. This may be repeated until an access path is determined for every combination of start and end points determined at steps S524 and S530, as well as the start and end points provided by the clinician.

Thereafter, or in instances where no alternative start and end points are desired, the method may skip to path C, and initiate step S534, where application 81 determines whether there are intervening structures obstructing any of the access paths 18 determined at step S520 or any of the alternative access paths determined at step S532. For example, application 81 may determine whether there are other airways, vascular and/or lymphatic structures or lumens or any of the other structures detected at step S504 obstructing any of the access paths 18. Additionally, application 81 may determine whether there are any such intervening structures that may not be obstructing an access path but are still in close proximity to an access path to create a risk of injury.

Next, at step S536, application 81 calculates a risk of injury to the intervening structures based on access path 18. The risk of injury may be based on the local physiology of the patient's lungs, i.e. the intervening structures detected at step S534, as well as the type of tissue through which access path 18 runs and the type of tools to be used. For example, the closer the proximity of an intervening structure to access path 18, the higher the risk of injury calculated for that access path. Similarly, while it is inherent that there will be some tissue damage regardless, damage to blood vessels greater than a certain size or certain types of tissue may want to be clearly avoided. Additionally, certain types of tools may be more or less likely to cause injury to certain types of tissue.

This process may be repeated until a risk of injury is calculated for each access path and alternative access path. Additionally, as noted above, the risk of injury may subsequently be recalculated and updated during navigation of tools 102, 104, 330 inside the patient's airways based on the detected location of the tools. A risk of injury may also be calculated for the treatment procedure itself, e.g. a biopsy, based on the selected access path 18 and end point 17 on target location 14. For example, application 81 may calculate a risk of injury for a biopsy based on the vasculature and tissue surrounding and interposed within target location 14. Such risk of injury for the treatment procedure may be combined with the risk of injury calculated for the access paths 18 and/or be maintained as a separate risk of injury.

Thereafter, at step S538, application 81 causes the display device to display the pathway generated at step S514, the access paths 18 determined at step S520, the alternative access paths determined at step S532, and the calculated risk of injury for each access path and alternative access path, on 3D model 12. The risk of injury may be displayed as a numerical value, such as a percentage or probability ratio, and/or as a graphical indicator, such as having the color in which access path 18 is displayed change according to the calculated risk for that access path. In an embodiment, the access paths 18 may be prioritized based on their associated risk of injury, and displayed to the user in order of their associated risk of injury. The risk of injury to target location 14 may also be displayed as combined with and/or separate from the risk of injury calculated for access path 18.

The clinician may review the displayed access paths 18 and their associated risk of injury, and may select, at step S540, a preferred access path 18 to be used during the treatment procedure. Alternatively, application 81 may determine which access path 18 has the lowest risk of injury, and may pre-select that access path 18 for the clinician's review and approval. Application 81 may update the pathway from the percutaneous entry point to start point 16 of the selected access path 18 if the point on the pleural surface to which the pathway was generated is different from start point 16 and start point 16 is not accessible from the pathway generated at step S514.

After an access path 18 is selected, application 81 determines, at step S542, whether the risk of injury calculated for that access path 18 is above a predetermined threshold. If the risk of injury is determined to be above the predetermined threshold, the method proceeds to step S524, where an alert is provided. The alert may be a graphical alert displayed on the display device, and/or an audible alert emitted by computing device 80. In some embodiments the clinician may be required to acknowledge the alert regarding the risk and effectively accept the risk.

Thereafter, or if it is determined that the risk of injury is not above the predetermined threshold, the method proceeds to step S546 where a determination is made if there are additional target locations for which access paths have to be determined. If there are additional target locations, the method returns to step S410. If there are no additional target locations, the method ends.

Figure 6:
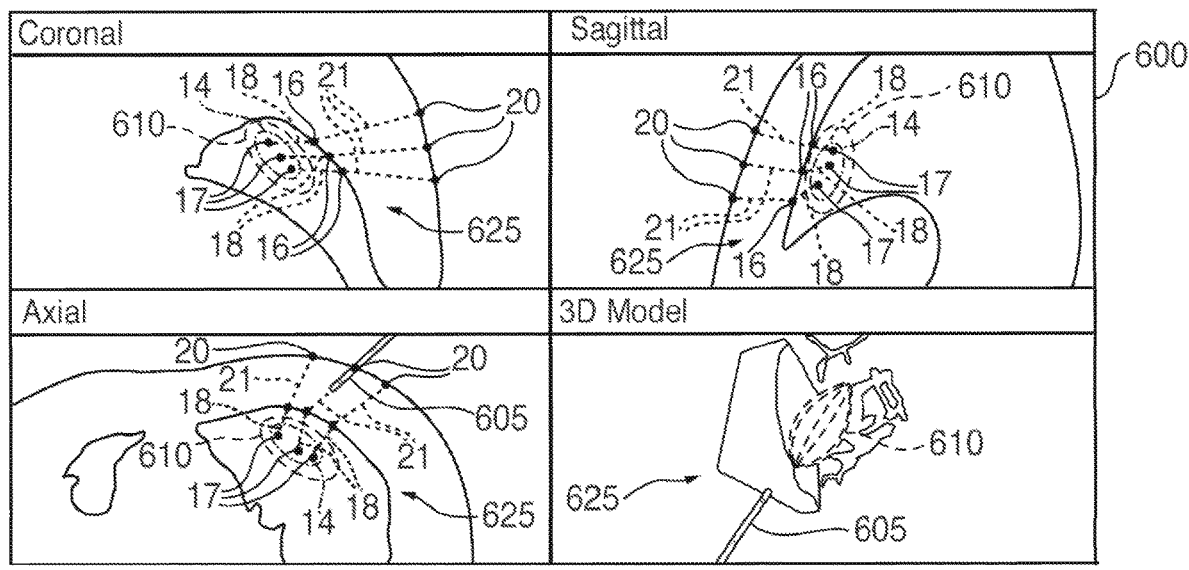
FIG. 6 shows an exemplary user interface for identifying access paths to a target location for a percutaneous surgical procedure, according to an embodiment of the present disclosure.

FIG. 6 shows an exemplary graphical user interface (GUI) 600 for identifying access paths to a target location for a percutaneous surgical procedure, according to an embodiment of the present disclosure. As with GUI 100 of FIG. 1, GUI 600 may be used by the clinician to review access paths, as well as their corresponding start and end points. As shown in FIG. 6, GUI 600 may show the patient's lungs 625 with target location 14 therein, along with various access paths 18 connecting start points 16 on the outer perimeter of lungs 625 with end points 17 on target location 14. GUI 600 also shows various insertion pathways 21 linking entry points 20 on the outside of the patient's body with start points 16 on the outer perimeter of lungs 625. GUI 600 further shows a digital tool 605 representing tool 330, and a projected ablation zone 610.

Figure 7:
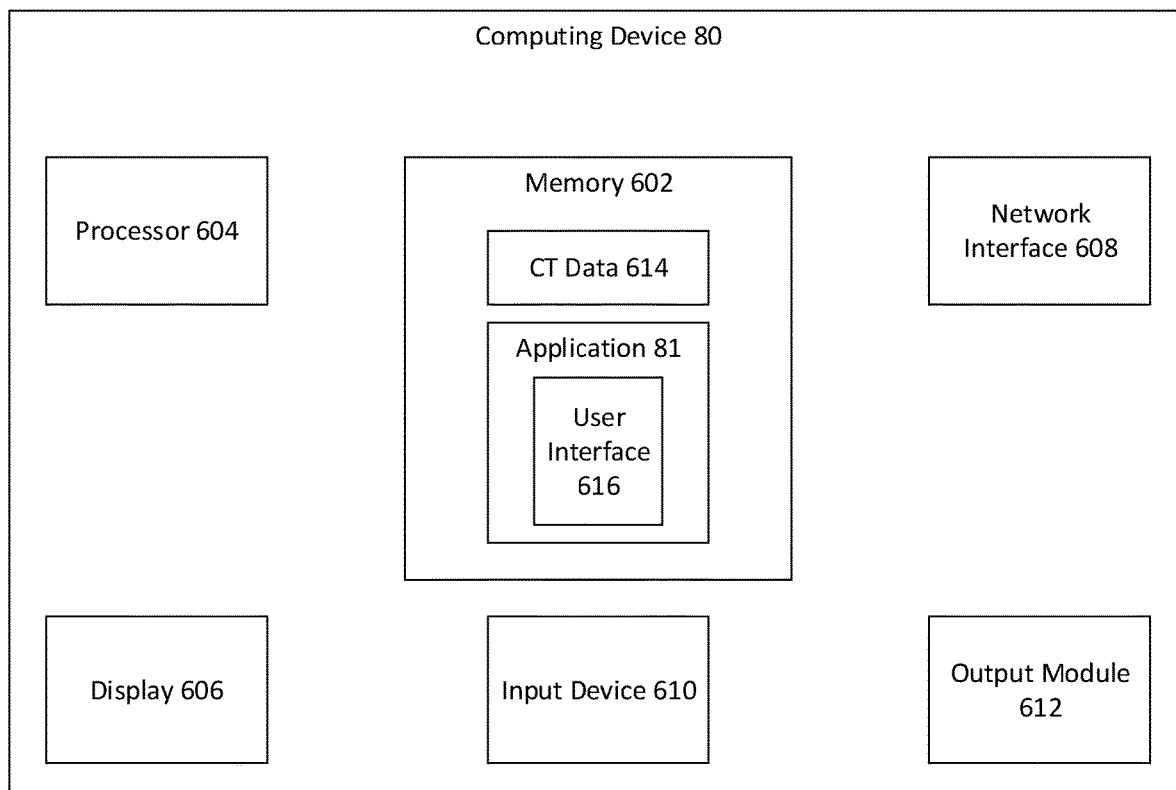
FIG. 7 is a schematic diagram of a computing device forming part of the EMN system of FIG. 2, which may be used to provide proximity awareness to pleural boundaries and vascular structures, according to an embodiment of the present disclosure.

With reference to FIG. 7, there is shown a simplified block diagram of computing device 80. Computing device 80 may include a memory 702, a processor 704, a display 706, a network interface 708, an input device 710, and/or an output module 712. Memory 702 may store application 81 and/or image data 714. Application 81 may, when executed by processor 704, cause display 706 to present user interface 716. Application 81 may also provide the interface between the sensed position of EM sensor 94 and the image and planning data developed in the pathway planning phase.

Detailed embodiments of devices, systems incorporating such devices, and methods using the same as described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in appropriately detailed structure. While the preceding embodiments are described in terms of bronchoscopy of a patient's airways, those skilled in the art will realize that the same or similar devices, systems, and methods may be used in other lumen networks, such as, for example, the vascular, lymphatic, and/or gastrointestinal networks as well.

With respect to memory 702 described above in connection with FIG. 7, the memory 702 may include any non-transitory computer-readable storage media for storing data and/or software that is executable by processor 704 and which controls the operation of computing device 80. In an embodiment, memory 702 may include one or more solid-state storage devices such as flash memory chips. Alternatively or in addition to the one or more solid-state storage devices, memory 702 may include one or more mass storage devices connected to the processor 704 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 704. That is, computer readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by computing device 80.

Network interface 708 may be configured to connect to a network such as a local area network (LAN) consisting of a wired network and/or a wireless network, a wide area network (WAN), a wireless mobile network, a Bluetooth network, and/or the internet. Input device 710 may be any device by means of which a user may interact with computing device 80, such as, for example, a mouse, keyboard, foot pedal, touch screen, and/or voice interface. Output module 712 may include any connectivity port or bus, such as, for example, parallel ports, serial ports, universal serial busses (USB), or any other similar connectivity port known to those skilled in the art.

Further aspects of image and data generation, management, and manipulation useable in either the planning or navigation phases of an EMN procedure are more fully described in commonly-owned co-pending U.S. Patent Publication No. 2016/0000414, entitled "METHODS FOR MARKING BIOPSY LOCATION", filed on Jun. 29, 2015, by Brown; U.S. Patent Publication No. 2016/0000517, entitled "INTELLIGENT DISPLAY", filed on Jun. 29, 2015, by Kehat et al.; U.S. Patent Publication No. 2016/0005224, entitled "UNIFIED COORDINATE SYSTEM FOR MULTIPLE CT SCANS OF PATIENT LUNGS", filed on Jul. 1, 2015, by Greenburg; U.S. Patent Publication No. 2016/0000303, entitled "ALIGNMENT CT", filed on Jul. 2, 2015, by Klein et al.; U.S. Patent Publication No. 2016/0005168, entitled "FLUOROSCOPIC POSE ESTIMATION", filed on May 29, 2015, by Merlet; and U.S. Patent Publication No. 2016/0000520, entitled "SYSTEM AND METHOD OF PROVIDING DISTANCE AND ORIENTATION FEEDBACK WHILE NAVIGATING IN 3D", filed on Jul. 2, 2015, by Lachmanovich et al., the contents of each of which are hereby incorporated by reference.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed is:

1. A non-transitory computer-readable storage medium storing instructions which, when executed by a processor, cause the processor to:
   generate a three-dimensional (3D) model of a patient's lungs;
   identify a point on a pleural surface of the patient's lungs with access to a target location in tissue of the patient's lungs from the 3D model;
   determine an access path between the target location and the identified point on the pleural surface;
   identify a percutaneous entry point on an exterior of the patient's body;
   generate an insertion pathway between the identified percutaneous entry point and a point on the pleural surface;
   determine if the point on the pleural surface of the generated insertion pathway is different from the identified point on the pleural surface of the access path;
   generate a second insertion pathway if it is determined that the point on the pleural surface of the generated insertion pathway is different from the identified point on the pleural surface of the access path;
   calculate a risk of injury to intervening structures between the target location and the identified point on the pleural surface of the access path, based on the access path;
   receive data describing a position of a surgical tool within a body of a patient; and
   cause movement of a surgical tool along at least one of the access path, the insertion pathway, or the second insertion pathway.

2. A method of planning a procedure for treatment of tissue in a patient's lungs, the method comprising:
   generating a three-dimensional (3D) model of the patient's lungs;
   displaying the 3D model of the patient's lungs;
   selecting a target location in the tissue of the patient's lungs as displayed on the 3D model;
   identifying a point on a pleural surface of the patient's lungs with access to the target location;
   determining an access path between the target location and the identified point on the pleural surface;
   identifying a percutaneous entry point on an exterior of the patient's body;
   generating an insertion pathway between the identified percutaneous entry point and a point on the pleural surface;
   determining if the point on the pleural surface of the generated insertion pathway is different from the identified point on the pleural surface of the access path;

generating a second insertion pathway if it is determined that the point on the pleural surface of the generated insertion pathway is different from the identified point on the pleural surface of the access path;

calculating a risk of injury to intervening structures between the identified point on the pleural surface of the access path and the target location, based on the access path;

determining if the calculated risk of injury is above a predetermined threshold;

generating an alert if the calculated risk of injury is determined to be above the predetermined threshold;

displaying at least one of the access path, the insertion pathway, a position of a surgical tool, or the calculated risk of injury for the access path on the 3D model; and causing movement of a surgical tool along at least one of the access path, the insertion pathway, or the second insertion pathway.

3. The method of claim 2, wherein the identified point on the pleural surface of the access path is a first identified point on the pleural surface and the access path is a first access path, and the method further comprises:

identifying a second point on the pleural surface with access to the target location;

determining a second access path between the target location and the second identified point on the pleural surface; and calculating a risk of injury to intervening structures between the target location and the second identified point on the pleural surface, based on the determined second access path, wherein displaying the first access path and the calculated risk of injury for the first access path on the 3D model further includes displaying the second access path and the calculated risk of injury for the second access path on the 3D model.

4. The method of claim 3, further comprising:

determining which of the first or second access paths has a lower calculated risk of injury; and selecting the access path that is determined to have a lower risk of injury.

5. The method of claim 3, further comprising receiving a user input selecting one of the first or second access paths.

6. The method of claim 2, wherein the identified point on the pleural surface of the access path with access to the target location is identified based on input received from a user.

7. The method of claim 6, further comprising:

identifying an alternative point on the pleural surface with access to the target location;

determining an alternative access path between the alternative point on the pleural surface and the target location; and calculating a risk of injury to intervening structures between the target location and the alternative point on the pleural surface, based on the determined alternative access path.

8. The method of claim 2, further comprising receiving a user input selecting a point on the target location as an end point for the access path, wherein the access path is determined between the identified point on the pleural surface of the access path and the point on the target location.

9. The method of claim 8, further comprising:

identifying an alternative point on the target location as an alternative end point for the access path;

determining an alternative access path between the identified point on the pleural surface of the access path and the alternative point on the target location; and calculating a risk of injury to intervening structures between the identified point on the pleural surface of the access path and the alternative point on the target location, based on the determined alternative access path.

10. The method of claim 2, further comprising displaying the alert if the calculated risk of injury is more than the predetermined threshold.

11. The method of claim 2, wherein the access path is represented by at least one of a straight line or a curved line.

12. The method of claim 2, further comprising using a tracking system to determine a position of a surgical tool in a body of a patient.

13. The method of claim 2, wherein the intervening structures are one or more of an airway wall, nerves, vascular lumens, vascular structures, lymphatic lumens, and lymphatic structures.

14. A navigation planning and procedure system comprising:

at least one processor; and a memory storing instructions that, when executed by the at least one processor, cause the at least one processor to:

generate a three-dimensional (3D) model of a patient's lungs;

select a target location in tissue of the patient's lungs from the 3D model;

identify a point on a pleural surface of the patient's lungs with access to the target location;

determine an access path between the target location and the identified point on the pleural surface;

identify a percutaneous entry point on an exterior of the patient's body;

generate an insertion pathway between the identified percutaneous entry point and a point on the pleural surface;

determine if the point on the pleural surface of the generated insertion pathway is different from the identified point on the pleural surface of the access path;

generate a second insertion pathway if it is determined that the point on the pleural surface of the generated insertion pathway is different from the identified point on the pleural surface of the access path;

calculate a risk of injury to intervening structures between the identified point on the pleural surface of the access path and the target location, based on the access path;

determine if the calculated risk of injury is above a predetermined threshold;

generate an alert if the calculated risk of injury is determined to be above the predetermined threshold;

cause a display device to display at least one of the access path, the insertion pathway, a position of a surgical tool, or the calculated risk of injury for the access path on the 3D model; and cause movement of a surgical tool along at least one of the access path, the insertion pathway, or the second insertion pathway.

15. The navigation planning and procedure system of claim 14, wherein the identified point on the pleural surface of the access path is a first identified point on the pleural surface and the access path is a first access path, and wherein the memory further stores instructions which, when executed by the at least one processor, cause the at least one processor to:

identify a second point on the pleural surface with access to the target location;

determine a second access path between the target location and the second identified point on the pleural surface; and calculate a risk of injury to intervening structures between the target location and the second identified point on the pleural surface, based on the determined second access path.

16. The navigation planning and procedure system of claim 15, wherein the memory further stores instructions which, when executed by the at least one processor, cause the at least one processor to:

determine which of the first or second access paths has a lower calculated risk of injury; and select the access path that is determined to have a lower risk of injury.

17. The navigation planning and procedure system of claim 14, wherein the identified point on the pleural surface of the access path with access to the target location is identified based on input received from a user.

18. The navigation planning and procedure system of claim 17, wherein the memory further stores instructions which, when executed by the at least one processor, cause the at least one processor to:

identify an alternative point on the pleural surface with access to the target location;

determine an alternative access path between the alternative point on the pleural surface and the target location; and calculate a risk of injury to intervening structures between the target location and the alternative point on the pleural surface, based on the determined alternative access path.

19. The navigation planning and procedure system of claim 14, wherein the memory further stores instructions which, when executed by the at least one processor, cause the at least one processor to receive a user input selecting a point on the target location as an end point for the access path, wherein the access path is determined between the identified point on the pleural surface of the access path and the point on the target location.

20. The navigation planning and procedure system of claim 14, wherein the memory further stores instructions which, when executed by the at least one processor, cause the at least one processor to:

identify an alternative point on the target location as an alternative end point for the access path;

determine an alternative access path between the identified point on the pleural surface of the access path and the alternative point on the target location; and calculate a risk of injury to intervening structures between the identified point on the pleural surface of the access path and the alternative point on the target location, based on the determined alternative access path.

* * * * *